United States Patent [19]

Beard

[11] Patent Number: 4,948,906

[45] Date of Patent: Aug. 14, 1990

[54] TRIMETHYLALUMINUM PROCESS

[75] Inventor: William R. Beard, Baton Rouge, La.

[73] Assignee: Ethyl Corporation, Richmond, Va.

[21] Appl. No.: 480,964

[22] Filed: Feb. 16, 1990

[51] Int. Cl.$^5$ ................................................ C07F 5/06
[52] U.S. Cl. ..................................................... 556/187
[58] Field of Search .......................................... 556/187

[56] References Cited

U.S. PATENT DOCUMENTS

| | | | |
|---|---|---|---|
| 4,349,483 | 9/1982 | Beach et al. | 556/187 |
| 4,364,872 | 12/1982 | Diefenbach | 556/187 |
| 4,364,873 | 12/1982 | Diefenbach | 556/187 |
| 4,364,874 | 12/1982 | Diefenbach | 556/187 |

*Primary Examiner*—Paul F. Shaver
*Attorney, Agent, or Firm*—David M. Bunnell; Joseph D. Odenweller

[57] ABSTRACT

Trimethylaluminum is made by reacting a methyl halide with a tri-$C_{2+}$ alkylaluminum, e.g. triethylaluminum, in the presence of a catalyst form by reacting bismuth metal with an alkylaluminum compound, e.g. trialkylaluminum, and an alkyl halide.

13 Claims, No Drawings

TRIMETHYLALUMINUM PROCESS

BACKGROUND

Unlike the ethyl and higher trialkylaluminum compounds which can be made economically by reactions of aluminum, hydrogen, and an olefin, trimethylaluminum has been produced only by processes which begin with a methyl halide. These include the direct reaction of a methyl halide with aluminum metal to form the methylaluminum sesquihalide, followed by a reduction step generally utilizing sodium as the reducing agent. Thus, starting with methyl chloride as a source of the methyl group:

$$3CH_3Cl + 2Al \rightarrow (CH_3)_3Al_2Cl_3$$

$$(CH_3)_3Al_2Cl_3 + 3Na \rightarrow (CH_3)_3Al + 3NaCl + Al$$

This process has been used on a commercial scale to produce trimethylaluminum. Processes of this type are described in an article by A. V. Grosse and J. M. Mavity, *Journal of Organic Chemistry*, 5, 106 (1940), and in U.S. Pat. Nos. 2,863,894 and 2,954,389.

U.S. Pat. No. 2,744,127 describes a related method involving the direct reaction of a 40Al/60 Mg alloy with a methyl halide, according to the equation:

$$6CH_3Cl + Al_2Mg_3 \rightarrow 2(CH_3)_3Al + 3MgCl_2$$

A method described in U.S. Pat. No. 2,839,556 does not use a reducing metal but is based on formation of cryolite as a means of removing halogen from a methylaluminum halide. For example, $$(CH_3)_2AlCl + NaF \rightarrow (CH_3)_2AlF + NaCl$$

$$3(CH_3)_2AlF + 3NaF \rightarrow 2(CH_3)_3Al + Na_3Al_2F_6$$

All of the above-described methods have the disadvantage of forming very large amounts of inorganic metal halide byproducts. These materials not only have very low value, but are also generally produced in forms which makes their recovery uneconomical. Hence they must be disposed of in a safe and ecologically acceptable manner, which adds further economic penalty to the trimethylaluminum synthesis.

Reviews of organoaluminum compound synthesis, e.g., in "Organoaluminum Compounds" by T. Mole and E. A. Jeffery (Elsevier, New York, 1972) describe other methods of trimethylaluminum synthesis generally not useful for economic commercial production. These include the initial preparation of a Grignard reagent, $CH_3MgX$, and its reaction with an aluminum halide in an ether solvent, $$3CH_3MgX + AlX_3 \rightarrow (CH_3)_3Al + 3MgX_2$$

which cannot be removed readily from the trimethylaluminum product. Another route, which has been of academic interest only, is initial synthesis of very toxic dimethylmercury (from a $CH_3MgX$ reagent), from which the mercury can be displaced by aluminum in a solvent-free reaction.

$$3(CH_3)_2Hg + 2Al \rightarrow 2(CH_3)_3Al + 3Hg$$

A recent U.S. Pat. No. 4,118,409, provides for jointly making trimethylaluminum and alkylaluminum bromides and iodides in an alkyl exchange process by mixing an aluminum trialkyl, such as triethylaluminum, and a methylaluminum bromide or iodide and then distilling from the mixture trimethylaluminum as a first fraction and then alkylaluminum bromides or iodides as a subsequent fraction.

Still more recently S. P. Diefenbach has described several methods for making trimethylaluminum from triethyl. In U.S. Pat. No. 4,364,872, triethylaluminum is reacted with a methyl halide in the presence of a catalyst formed from a bismuth compound, e.g. $BiCl_3$. The reaction is conducted in an autoclave.

Diefenbach U.S. Pat. No. 4,364,873 describes a similar process using a catalyst formed from a vanadium compound (e.g. $VOCl_3$), a trialkylaluminum (e.g. triethylaluminum) and an alkyl iodide.

Diefenbach U.S. Pat. No. 4,364,474 describes a trimethylaluminum process using a non-catalyzed alkyl exchange between a higher trialkylaluminum such as triethylaluminum and methyl iodide.

SUMMARY

It has now been discovered that trimethylaluminum can be made by reacting a methyl halide with a higher trialkylaluminum in the presence of a catalyst formed by reacting finely divided bismuth metal, an alkylaluminum and an alkyl halide.

DESCRIPTION OF THE PREFERRED EMBODIMENT

A preferred embodiment of the invention is a process for making trimethylaluminum, said process comprising reacting a methyl halide selected from methyl chloride, methyl bromide, methyl iodide and mixtures thereof with a tri-$C_{2+}$ alkylaluminum or mixture thereof in the presence of a catalyst formed by the reaction of bismuth metal with a trialkylaluminum and an alkyl halide.

The present process is an improvement in the process described by Diefenbach U.S. Pat. No. 4,364,872 and provides a different, less costly catalyst than that used in Diefenbach, et al.

The catalyst is formed by reacting metallic bismuth with an alkylaluminum compound and an alkyl halide. The bismuth metal should be finely divided. Both bismuth turnings and particles have been used. Particles finer than 100 mesh, e.g. 100–400 mesh, are preferred. Good results have been achieved using 100mesh bismuth particles.

Alkylaluminum compounds that can be used to make the catalyst include any compound having at least one alkyl-Al bond. Some examples of these are diethylaluminum ethoxide, diethylaluminum chloride, ethylaluminum dibromide, ethylaluminum sesquichloride, diisobutylaluminum hydride and the like.

Useful tri-$C_{2+}$ alkylaluminum compounds are triethylaluminum, tri-n-propylaluminum, tri-n-butylaluminum, triisobutylaluminum, tri-n-hexylaluminum, tri-n-octylaluminum and mixtures thereof. Also included are the mixed alkylaluminums such as n-propyl diethylaluminum, diisobutyl ethylaluminum and the like. The most preferred tri-$C_{2+}$ alkylaluminum reactants are the tri-$C_{2-4}$ alkylaluminums. The most preferred alkylaluminum reactant is triethylaluminum.

Any low molecular weight alkyl halide can be used to prepare the catalyst. Preferably the alkyl is a $C_{1-4}$ alkyl. Examples are methyl chloride, methyl bromide, ethyl bromide, ethyl iodide, n-butyl bromide and the like. The more preferred alkyl halides used in catalyst preparation are methyl chloride and bromide, especially methyl bromide.

A solvent can be included in the reaction mixture. Useful solvents include the inert liquid aliphatic hydrocarbons such as hexane, octane, decane, cyclohexane, cyclooctane. Aromatics such as benzene, toluene, xylene and the like can be used although this may lead to some aromatic substitution.

The ratio of the bismuth/alkyl aluminum/alkyl halide used to make the catalyst can vary widely. A useful range is 1-2 gram atoms bismuth/1-100 gram moles of aluminum alkyl/1-1000 gram moles of alkyl halide. A more preferred ratio is 2 g atoms Bi/100 g mol Al-alkyl/325 g moles of alkyl halide, with an inert diluent solvent such as an alkane included so that the solvent comprises about 35 weight percent of the mixture. The catalyst may be isolated by distilling the alkyl halides from the reaction mixture whereupon two liquid phases form with the active catalyst being contained in the more dense phase.

The catalyst can be separately prepared by forming the above described mixture and heating the mixture to about 30°–200° C. A preferred way to prepare the catalyst is by charging a reaction vessel with bismuth metal, then adding the tri-$C_{2+}$ alkylaluminum reactant and the solvent while stirring under nitrogen, and then heating to 100°–150° C. while injecting the methyl halide reactant below the liquid surface. The catalyst will form in situ after a short period, e.g. 5–60 minutes, and the alkyl exchange reaction will commence.

The amount of bismuth in the reaction mixture need only be a catalytic amount. This is expressed in terms of the ratio of gram atoms of bismuth per gram mole of initial tri-$C_{2+}$ alkylaluminum. A useful ratio is about 0.0025–0.1/1.0. Good results have been achieved using 0.01 gram atoms of bismuth per gram mole of tri-$C_{2-4}$ alkylaluminum. A small amount of iodine may be included to activate the bismuth.

The tri-$C_{2+}$ alkylaluminum, bismuth metal or preformed bismuth catalyst and methyl halide can be all charged to a nitrogen-purged pressure reaction vessel (e.g. an autoclave) at the start of the reaction. The reactor can then be sealed and heated to reaction temperature while stirring. A reaction period of about 0.5–12 hours usually suffices to achieve equilibrium. The autoclave can then be cooled and vented. The contents are then distilled to recover trimethylaluminum.

In another mode of operation, the process can be carried out by placing all of the tri-$C_{2+}$ alkylaluminum reactant and the bismuth metal or pre-formed bismuth catalyst in a reaction vessel under an inert atmosphere such as nitrogen and then stirring and heating to reaction temperature. Methyl halide is then introduced into the liquid phase at a controlled rate such that an excessive amount of methyl halide does not collect in the reactor. Methyl halide feed usually requires about 0.25–12 hours depending on reaction scale. Most of the methyl halide will react with the tri-$C_{2+}$ alkylaluminum under these condition to form trimethylaluminum and $C_{2+}$ alkyl halide. The reaction temperature is preferably high enough such that this $C_{2+}$ alkyl halide will vaporize from the reaction mixture. For example, ethyl chloride has a normal boiling point of 12.3° C., ethyl bromine 38.4° C. and n-butyl chloride 78.5° C.

In this continuous methyl halide feed mode of operation, the reaction is conducted at atmospheric pressure or close to atmospheric pressure so the lower $C_{2+}$ alkyl halide that forms will readily vaporize. Part of the methyl halide will also escape the liquid reaction phase and be conducted from the reaction vessel together with the $C_{2+}$ alkyl halide. In practice about 4–5 moles of methyl halide will be injected into the liquid reaction phase to convert one mole of tri-$C_{2+}$ alkylaluminum to trimethylaluminum. The vented methyl halide and $C_{2+}$ alkyl halide can be condensed and separated by conventional means.

Progress of the reaction can be monitored by periodically withdrawing small samples and analyzing them. When the reaction is complete, trimethylaluminum can be recovered from the reaction mixture by fractionation. Trimethylaluminum has a normal boiling point of 127° C., so the distillation can be conducted at atmospheric pressure. If desired, the fractionation can be conducted at reduced pressure if the system is leakproof.

Another mode of operation comprises:

(A) forming a catalyst mixture in a reaction zone by reacting a trialkylaluminum with bismuth metal and an alkyl halide, (B) continuously feeding to said reaction zone (i) trialkyl aluminum wherein the alkyl groups contain at least two carbon atoms and (ii) at least a stoichiometric amount, based on the formation of trimethylaluminum, of a methyl halide whereby said trialkylaluminum feed and said methyl halide react to form trimethylaluminum and a $C_{2+}$ alkyl halide, (C) continuously distilling said $C_{2+}$ alkyl halide and any unreacted methyl halide from said reaction zone and (D) recovering trimethylaluminum from said reaction zone.

In this embodiment the reactants and catalysts are the same as in the previous embodiment. It differs in that both the methyl halide and tri-$C_{2+}$ alkylaluminum are continuously fed to the reaction zone which contains the catalyst. The catalyst is preferably formed in the reaction zone by combining a trialkylaluminum and bismuth metal in an aliphatic hydrocarbon solvent having at boiling point above the reaction temperature. Normal decane (b.p. 174° C.) is a preferred solvent. The mixture is stirred and heated to reaction temperature and then both tri-$C_{2+}$ alkylaluminum, e.g. triethylaluminum, and methylhalide are concurrently fed to the reaction zone at a controlled rate. The methyl halide is preferably injected into the liquid phase. A preferred mole ratio of methyl halide to tri-$C_{2+}$ alkylaluminum is about 3–6:1 and more preferably about 4–5:1.

The methyl halide enters into an alkyl exchange reaction with the tri-$C_{2+}$ alkylaluminum forming trimethylaluminum and $C_{2+}$ alkyl halide. The $C_{2+}$ alkyl halide will vaporize at the reaction temperature and be conducted out of the reaction zone. As before, a portion of the methyl halide will escape the liquid phase and pass but of the reactor together with the $C_{2+}$ alkyl halide. This is why a stoichiometric excess of methyl halide is used.

After the addition of the tri-$C_{2+}$ alkylaluminum and methyl halide is complete, the mixture is stirred at reaction temperature and then analyzed to be sure most of the tri-$C_{2+}$ alkylaluminum has been converted to trimethylaluminum. Trimethylaluminum can then be recovered from the reaction mixture by fractionation.

The process can also be conducted in a continuous manner comprising:

(A) forming a catalyst mixture in a reaction zone by reacting a trialkylaluminum, bismuth metal and an alkyl halide, (B) continuously feeding to said reaction zone (i) trialkylaluminum wherein the alkyl groups contain at least two carbon atoms and (ii) at least a stoichiometric amount, based on the formation of trimethylaluminum, of a methyl halide whereby said trialkylaluminum feed and said methylhalide react to form trimethylaluminum and a $C_{2+}$ alkyl halide, (C) continuously distilling said trimethylaluminum, said $C_{2+}$ alkyl halide and any unreacted methyl halide from said reaction zone and, (D) recovering trimethylaluminum from the distillate.

This embodiment of the process uses the same reactants and catalyst as the previous embodiment. It also uses the same concurrent addition of both methyl halide and tri-$C_{2+}$ alkylaluminum to the reaction zone using a stoichiometric excess of methyl halide. It differs in that the reaction temperature and pressure are such that the trimethylaluminum formed in the reaction distills out together with the $C_{2+}$ alkyl halide and any unreacted methyl halide. Since trimethylaluminum has a normal boiling point of about 127° C., it is preferred to conduct this embodiment above 127° C., for example 130–175° C., more preferably 135°–150° C. Optionally the process can be conducted at reduced pressure to lower the boiling point of trimethylaluminum. Reduced pressure operation is not preferred because of the hazards of any air leak into the reaction system which could lead to a violent reaction.

The continuous process can also be conducted with an inert solvent in the reaction zone which boils higher than trimethylaluminum. Aliphatic hydrocarbons such as n-decane are preferred.

The vapor removed is preferably condensed in two stages. The first condenser is operated at a temperature such that the trimethylaluminum condenses but not the alkyl halides. The alkyl halides are then condensed downstream in a second condenser operated at a lower temperature.

The following Examples serve to show how the process is carried out.

EXAMPLE 1

A nitrogen-purged dry reactor was charged with 17.37 g decane, 0.3 g of 100-mesh bismuth metal and 8.58 g triethylaluminum. The reactor was sealed, cooled to −196° C. and evacuated after which 22.0 g of methyl bromide was introduced into the reactor. The sealed reactor was then heated to 120° C. in an oil bath and held at 120° C. for 1.5 hours.

The reactor was cooled to −196° C. and attached to the bottom of a low-temperature, high vacuum fractional distillation column.[1] The reaction products were then distilled out of the reactor and into the column with the top of the column held at −65° C. The distillation was continued for about seven hours after which material was distilling at a very slow rate.

[1]"The Manipulation of Air-Sensitive Compounds," second edition, by D. F. Shriver and M. A. Drezdzon. 1986. John Wiley and Sons, Inc. New York, p. 194.

Analysis of the product fractions showed that 49 mmol of TMA and 7.9 mmol of dimethylaluminum bromide were produced: 9.8 mmol of TEA remained.

EXAMPLE 2

This example used recycled catalyst. The reaction vessel from Example 1, after distilling the volatile components from the reactor, leaving the catalyst layer in the reactor, was recharged with 17.33 g decane and 8.57 g (75.1 mmol) triethylaluminum. In the same manner as Example 1, it was charged with 21.7 g methyl bromide and reacted at 120° C. for 1 hour. The product mixture was distilled under high vacuum as in Example 1 to recover 60 mmol trimethylaluminum, 5.4 mmol of dimethylaluminum bromide and 4.7 mmol unreacted triethylaluminum.

EXAMPLE 3

This reaction was conducted in the same manner as Example 1 using 1.38 g decane and 0.31 g bismuth metal. A small amount of iodine (0.02 g) was also added followed by 8.57 g (75.1 mmol) triethylaluminum. The vacuum-distilled product contained 56 mmol trimethylaluminum, 7.2 mmol dimethylaluminum bromide and 9.8 mmol unconverted triethylaluminum.

EXAMPLE 4

This example used recycled catalyst from Example 3. After removal of the upper product layer from the reaction vessel of Example 3, the vessel was recharged with 17.29 g decane, 8.61 g triethylaluminum (75.4 mmol) and 22.7 g of methyl bromide. After a one hour reaction at 120° C., the products were distilled under high vacuum as in Example 1 and were found to contain 63 mmol of trimethylaluminum, 5.2 mmol of dimethylaluminum bromide and only 1.0 mmol triethylaluminum.

As shown by the above examples, the present invention provides a relatively inexpensive process for making trimethyl directly from a readily available tri-higher alkylaluminum such as triethylaluminum.

I claim:

1. A process for making trimethylaluminum, said process comprising reacting a methyl halide selected from methyl chloride, methyl bromide, methyl iodide and mixtures thereof with a tri-$C_{2+}$ alkylaluminum or mixture thereof in the presence of a catalyst formed by the reaction of bismuth metal with an alkylaluminum compound and an alkyl halide.

2. A process of claim 1 wherein said alkylaluminum compound is a trialkylaluminum.

3. A process of claim 2 wherein said tri-$C_{2+}$ alkylaluminum is triethylaluminum.

4. A process of claim 3 wherein said methyl halide is methyl chloride.

5. A process of claim 3 wherein said methyl halide is methyl bromide.

6. A process of claim 3 conducted at a temperature of about 30°–180° C.

7. A process of claim 6 conducted in a closed pressure reaction vessel.

8. A process of claim 7 wherein said methyl halide is methyl bromide.

9. A process of claim 6 conducted by feeding said methyl halide into the liquid phase of said triethylaluminum over a period of about 0.25–12 hours.

10. A process of claim 9 wherein ethyl halide formed in the reaction is allowed to vent from the reaction vessel.

11. A process of claim 10 wherein said methyl halide is methyl bromide.

12. A process of claim 11 wherein the reaction temperature is in the range of 30°–180° C.

13. A process of claim 12 wherein said reaction temperature is about 90°–130° C.

* * * * *